United States Patent [19]
Brun et al.

[11] Patent Number: 5,399,750
[45] Date of Patent: Mar. 21, 1995

[54] PREPARATION OF MALEAMIC ACID

[75] Inventors: Daniel Brun, Charly; Pierre-Yves Lahary, Lyons, both of France

[73] Assignee: Rhone-Poulenc Chimie, Courbevoie, France

[21] Appl. No.: 184,351

[22] Filed: Jan. 21, 1994

[30] Foreign Application Priority Data

Jan. 20, 1993 [FR] France ................... 93 00511

[51] Int. Cl.$^6$ ........................................... C07C 205/00
[52] U.S. Cl. ............................................... 562/553
[58] Field of Search ......................................... 562/553

[56] References Cited

U.S. PATENT DOCUMENTS

| | | |
|---|---|---|
| 2,459,964 | 1/1949 | Robinson et al. |
| 3,336,384 | 8/1967 | Gee ........................... 562/553 |
| 4,839,461 | 6/1989 | Boehmke ................... 562/553 |

OTHER PUBLICATIONS

Database WPI, Section Ch, Week 7438, Derwent Publications Ltd., London, GB; Class E10, AN 74-66969V (Nippon Shikubai Kagaku) (1974).
Database WPI, Section CH, Week 7335, Derwent Publications Ld., London, GB; Class E10, AN 73-49652U (Yu G Mamedaliev) (1973).
Chemical Abstracts, vol. 79, 1973, Columbus, Ohio, abstract No. 52751w, p. 319.

Primary Examiner—Michael L. Shippen
Attorney, Agent, or Firm—Burns, Doane, Swecker & Mathis

[57] ABSTRACT

Maleamic acid (aminomaleic acid) is improvedly prepared by reacting gaseous ammonia with molten maleic anhydride under reactant contact conditions of high surface area, for example reacting said gaseous $NH_3$ with a thin film of said molten maleic anhydride or with said molten maleic anhydride in a state of vigorous agitation.

15 Claims, No Drawings

PREPARATION OF MALEAMIC ACID

BACKGROUND OF THE INVENTION

1. Field of the Invention

The present invention relates to the preparation of maleamic acid, and, more especially, to the preparation of maleamic acid by reacting maleic anhydride with ammonia under conditions of optimal contact surface area.

2. Description of the Prior Art

Maleamic acid is conventionally prepared by reacting maleic anhydride with ammonia. The maleic anhydride is employed either in a soluble state or in the vapor phase.

JP-74/35,325 more particularly describes such a process, carried out in an organic solvent medium at a temperature which ranges from room temperature to 100° C. The ammonia is introduced in gaseous state within the solvent. A subsequent isolation stage provides the expected product.

Maleic anhydride, when heated to at least its vaporization temperature, namely, at least 215° C., with gaseous ammonia, also produces maleamic acid. However, this reaction requires the presence of a catalyst. This may be, in particular, a mixture of $V_2O_5$, $P_2O_5$ and $Al_2O_3$ (USSR 36,282).

SUMMARY OF THE INVENTION

A major object of the present invention is the provision of an improved and more economical process for the preparation of maleamic acid vis-a-vis those processes hitherto known to this art.

Indeed, it has now been determined that maleic anhydride can be effectively reacted with gaseous ammonia in the absence of any organic solvent and of any catalyst. The use of maleic anhydride in a molten state permits the presence of these two compounds to be avoided.

Briefly, the present invention thus features a process for the preparation of maleamic acid by reacting maleic anhydride with gaseous ammonia, wherein the maleic anhydride is in a molten state and is contacted with the gaseous ammonia under conditions such that the contact surface area between the two compounds is optimized.

DETAILED DESCRIPTION OF BEST MODE AND PREFERRED EMBODIMENTS OF THE INVENTION

More particularly according to the present invention, the subject process presents the advantage of directly producing maleamic acid without requiring subsequent purification stages of the filtration and concentration type. This is of primary interest, both at the economic level and at the level of conducting the process on an industrial scale.

Furthermore, the supplementary presence of an organic solvent and/or of a catalyst is not required.

In the process according to the invention, the maleic anhydride is first heated to a temperature of from about its melting point, namely, 50° C., to 150° C., and more particularly from 60° to 130° C., in a preferably anhydrous and deoxygenated reaction medium. It will be appreciated that the maleic anhydride may be melted via any heating means.

Any technical means can be employed for increasing the contact surface between the two compounds, in order to optimize the reaction between the molten maleic anhydride and the ammonia.

Representative operating conditions which favor intimate contact between the two components can be established, in particular, by vigorous agitation of the reactor or reaction vessel containing the maleic anhydride in molten state. Such agitation from the corresponding centrifugal force uniformly disperses the mass of molten maleic anhydride on the inner face surface of the walls of the reactor, in a thin film of very reduced thickness. A high contact surface area between the maleic anhydride thus dispersed and the ammonia injected into the reactor is thus ensured.

Many and varied apparatuses/means are known to this art for promoting contact between the two reagents. These can be stirred reactors, dryers, atomizers, and the like.

The reaction between the molten maleic anhydride and the ammonia is preferably carried out in an anhydrous reaction medium and at a temperature compatible with melting of said anhydride. This temperature preferably ranges from about 50° to 150° C., preferably from 60° to 130° C.

In a preferred embodiment of the invention, the gaseous ammonia is introduced continuously onto the surface of the thin film of molten maleic anhydride.

According to the present invention, the gaseous ammonia is introduced either alone or in admixture with an inert gas, particularly argon or nitrogen. The introduction of the ammonia in admixture with an inert gas is of particular interest as it permits better control of the reaction temperature.

In another preferred embodiment of the invention, the maleic anhydride, introduced into a container of the reactor type, for example, in previously deoxygenated form, is heated to a temperature of greater than or equal to its melting point, but still below 150° C. It is preferably heated to from 60° to 130° C. Since the maleic anhydride is in molten state, a stream or current of gaseous ammonia is circulated within the container/reactor at a controlled rate. To optimize the contact surface between the maleic anhydride and the ammonia, the reaction mixture is agitated vigorously, preferably mechanically. The progress of the reaction is monitored using a temperature sensor and a flowmeter for $NH_3$. The duration of the reaction is of course a function of the flow rate at which the amount of gaseous ammonia required for conversion of the maleic anhydride into maleamic acid is introduced. At the end of the reaction, the expected maleamic acid is collected directly, in a virtually quantitative yield and at a very satisfactory purity.

The maleamic acid thus prepared is, inter alia, a useful starting material for the synthesis of polysuccinimide and/or polyaspartic acid.

In order to further illustrate the present invention and the advantages thereof, the following specific example is given, it being understood that same is intended only as illustrative and in nowise limitative.

EXAMPLE 6.4 g of solid maleic anhydride were introduced into a glass three-necked reactor of 100 ml volume, fitted with a scraping anchor stirrer and a temperature probe. After having flushed the entire device with nitrogen, the reactor was introduced into an oil bath which had been preheated to 80° C. When the maleic anhydride had melted, vigorous stirring was initiated such that it was uniformly spread as a thin layer on the internal walls of the reactor.

When the temperature within the reactor reached 80° C., a gaseous stream, at room temperature, of a mixture of ammonia and nitrogen, in a ratio of 0.85 by volume, was introduced. 1.11 g of ammonia, corresponding to the stoichiometric amount, were thus introduced over the course of 51 minutes.

7.35 g of a white solid were obtained, i.e., a yield of 97.9%, which had the following characteristics:

I.R.: 3,383 cm$^{-1}$, 3,208 cm$^{-1}$ (NH$_2$); 1,715 cm$^{-1}$ (acid CO); 1,618 cm$^{-1}$ (amide CO); Differential thermal analysis (10° C./minute): 1 endothermal fusion peak at 170° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of maleamic acid, comprising reacting gaseous ammonia with molten maleic anhydride under reactant contact conditions of high surface area.

2. The process as defined by claim 1, carried out at a temperature ranging from 50° to 150° C.

3. The process as defined by claim 2, carried out at a temperature ranging from 60° to 130° C.

4. The process as defined by claim 1, carried out in the absence of organic solvent and/or a catalyst.

5. The process as defined by claim 1, said gaseous ammonia comprising admixture thereof with an inert gas.

6. The process as defined by claim 5, said inert gas comprising nitrogen.

7. The process as defined by claim 1, comprising reacting gaseous ammonia with a thin film of said molten maleic anhydride.

8. The process as defined by claim 1, comprising reacting gaseous ammonia with vigorously agitated molten maleic anhydride.

9. The process as defined by claim 1, carried out in a reactor provided with means for enhancing the surface area of contact between the reactants contained therein.

10. The process as defined by claim 9, said reactor comprising stirring means.

11. The process as defined by claim 9, said reactor comprising an atomizer.

12. The process as defined by claim 9, said reactor comprising drying means.

13. The process as defined by claim 1, consisting essentially of reacting gaseous ammonia with molten maleic anhydride.

14. The process as defined by claim 1, carried out in an anhydrous and deoxygenated reaction medium.

15. The process as defined by claim 1, comprising directly preparing said maleamic acid.

* * * * *